United States Patent
Yi et al.

(10) Patent No.: US 9,483,870 B2
(45) Date of Patent: Nov. 1, 2016

(54) APPARATUS FOR PROCESSING, GENERATING, STORING AND DISPLAYING IMAGES IN PICTURE ARCHIVING COMMUNICATION SYSTEM, AND METHOD THEREOF

(71) Applicant: Infinitt Healthcare Co. Ltd., Seoul (KR)

(72) Inventors: Jae Youn Yi, Seoul (KR); Jin Kook Kim, Seoul (KR); Byeong Soo Kim, Gyeonggi-Do (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 476 days.

(21) Appl. No.: 13/870,513

(22) Filed: Apr. 25, 2013

(65) Prior Publication Data

US 2013/0335408 A1 Dec. 19, 2013

(30) Foreign Application Priority Data

Apr. 27, 2012 (KR) .................. 10-2012-0044581

(51) Int. Cl.
  *G06T 17/00* (2006.01)
  *G06F 19/00* (2011.01)
  *G06T 19/00* (2011.01)

(52) U.S. Cl.
  CPC ............ *G06T 17/00* (2013.01); *G06F 19/321* (2013.01); *G06T 19/00* (2013.01); *G06T 2210/41* (2013.01)

(58) Field of Classification Search
  None
  See application file for complete search history.

(56) References Cited

U.S. PATENT DOCUMENTS

| | | | |
|---|---|---|---|
| 7,512,279 B2 | 3/2009 | Schoisswohl | |
| 8,041,129 B2 | 10/2011 | Ernvik et al. | |
| 8,094,894 B2 | 1/2012 | Nagler et al. | |
| 8,105,080 B2 | 1/2012 | Chishti et al. | |
| 8,107,701 B2 | 1/2012 | Shirahata et al. | |
| 8,107,708 B2 | 1/2012 | Hoppe et al. | |
| 8,125,480 B2 | 2/2012 | Schiwietz et al. | |
| 8,135,111 B2 | 3/2012 | Jaffray et al. | |
| 8,135,198 B2 | 3/2012 | Lachaine et al. | |
| 8,145,292 B2 | 3/2012 | Vining | |
| 8,150,111 B2 | 4/2012 | Borland et al. | |
| 8,447,383 B2 | 5/2013 | Hyun et al. | |
| 2006/0204069 A1* | 9/2006 | Le Bras | A61B 6/505 382/132 |
| 2010/0215237 A1* | 8/2010 | Ohishi | A61B 6/507 382/131 |

FOREIGN PATENT DOCUMENTS

| | | |
|---|---|---|
| JP | 2008-193693 A | 8/2008 |
| KR | 10-2010-0119224 A | 11/2010 |
| KR | 10-2011-0013738 | 2/2011 |
| WO | WO-2007/122896 | 11/2007 |

OTHER PUBLICATIONS

Edelsbrunner, H. et al., "Wrapping 3D Scanning Data," SPIE, vol. 3313, pp. 148-158.
Ohbuchi, R. et al., "Incremental Volume Rendering Algorithm for Interactive 3D Ultrasound Imaging," Dept. of Computer Sci., Univ. N.C. at Chapel Hill, pp. 486-500.

* cited by examiner

*Primary Examiner* — Said Broome
(74) *Attorney, Agent, or Firm* — Mintz Levin Cohn Ferris Glovsky and Popeo, P.C.; Kongsik Kim; Jonathon Western

(57) ABSTRACT

Disclosed are an apparatus and method for storing and displaying images in a picture archiving and communication system (PACS). The apparatus, comprising: a processor configured to: generate a two-dimensional (2D) medical image for a three-dimensional (3D) medical image at each of reference points of a predetermined (3D) screen model; and store the generated (2D) medical image along with attribute information related to the generation of the (2D) medical image to a storage device or a memory.

21 Claims, 17 Drawing Sheets

APPARATUS FOR PROCESSING, GENERATING, STORING AND DISPLAYING IMAGES IN PICTURE ARCHIVING COMMUNICATION SYSTEM, AND METHOD THEREOF

CROSS-REFERENCE TO RELATED APPLICATION

This application claims under 35 U.S.C. §119(a) the benefit of Korean Application No. 10-2012-0044581 filed Apr. 27, 2012, which is incorporated herein by reference.

TECHNICAL FIELD

The present invention relates, in general, to the storage and display of medical images and, more particularly, to a method and apparatus for generating, storing, and displaying medical images, which enable three-dimensional (3D) medical images to be easily displayed on a client terminal.

BACKGROUND ART

In general, in medical activities where the lives of patients are concerned, clinical diagnosis occupies an important role in the treatment of such patients. The development of medical technology is very beneficial in helping medical professionals to perform precise clinical diagnoses, and it is expected that dependency on the development of medical technology will increase.

Modality or medical imaging apparatus, such as Computer Tomography (CT) equipment and Magnetic Resonance Imaging (MRI) equipment, has become essential equipment in modern medicine. In current medical procedures, however, an image of an abnormal body part of a patient is captured by pieces of modality, and the captured image is printed out in a film form and transferred to the physician in charge of the patient. Accordingly, a lot of time and manpower are necessary to make a final clinical diagnosis, which leads to inefficient resource management and wasted hospital funds. Additionally, rapid and precise treatment cannot be provided to a patient.

Furthermore, in Korea, the statute provides that an X-ray film must be kept for 5 years. In each hospital, X-ray films are classified and stored in accordance with patients. As the size of a hospital and the number of patients increase, the number of X-ray films to be maintained also increases. This results in several problems, such as the waste of space and manpower due to the storing and management of X-ray films, films being damaged due to poor storage or management, necessary re-photographing due to the loss of films, medical disputes over the loss of films, and the waste of time and manpower necessary to locate stored films.

Meanwhile, with the development of computers and communication technology, systems for providing medical service using computers and data communication technology have been researched and developed even in the medical field in which the lives of patients are handled. For example, a picture archiving and communication system (PACS) in which a computer communication network is installed throughout the entire hospital, all X-ray films are converted into digital data and put into a database, the digital data is stored in a high-capacity storage medium connected to a server, and the X-ray images of a desired patient can be checked in each doctor's office through a computer monitor if necessary, has recently been introduced.

PACS is a comprehensive digital image management system and transmission system for retrieving medical images, in particular, radiologic diagnostic images in a digital form, storing the medical images in a digital data form instead of the typical X-ray film form, sending the medial images over a high-speed communication network, and allowing radiologists and clinicians to treat patients using an image inquiry device instead of the existing film view box.

The ultimate goal of PACS is to construct a filmless hospital system. To this end, techniques, such as image display and processing, data communication and networking, a database, information management, a User Interface (UI), and data storage and management, must be comprehensively constructed.

Communication in PACS is performed using Digital Imaging and Communications in Medicine (DICOM) protocol as a standard. The DICOM protocol refers to a communication protocol that efficiently supports communication between various digital image acquisition apparatuses, such as those used in CT, MRI, nuclear medicine, and ultrasonic waves, and other information systems using an industry standard network. The communication protocol was developed and jointly standardized by the American College of Radiology (ACR) and the National Electrical Manufacturers Association (NEM) in 1984. In 1985, the first standard of the communication protocol was established.

Thereafter, the communication protocol underwent two revisions, in 1988 and 1993, and thus reached the current version 3.0, which has become called DICOM.

The background of the DICOM protocol lies in that as the medical industry becomes information-oriented, modalities have typically been used in conjunction with each other, rather than being used independently, and there is a need for agreement in exchanging medical images and corresponding information between modalities.

That is, in the past, unless manufacturers purchased expensive gateways, communication between the manufacturers was impossible, because the manufacturers employed different methods of storing and communicating information depending on the type and model of modality, and no specific standard was adhered to.

Now that the DICOM standard has been established, however, manufacturers that comply with the DICOM standard can exchange information without the need for special gateways, irrespective of their modality. This means that communication with remote places has become possible, in addition to communication between modalities supporting the DICOM standard within a hospital.

Furthermore, since a standard method widely being used in the computer industry is used as a network configuration method for the DICOM standard, the DICOM standard can be easily applied to connections within a hospital, communication between remote clinics, and all medical image-related systems including remote diagnostic systems.

In general, a radiologist chiefly uses thin-slice data for generating a three-dimensional (3D) medical image, and a clinician chiefly uses thick-slice data for generating a two-dimensional (2D) medical image.

In a clinical medicine department that requires medical procedures and operations, requests for 3D functionality using thin-slice data are increasing, but an image captured in a radiology department is sent to the clinical medicine department because it is difficult to use the thin-slice data directly in the clinical medicine department due to limits, such as a data storage limit and a limited transmission bandwidth. However, there is a problem in that the captured image can be used only limitedly because it cannot be three-dimensionally rotated for a viewpoint desired by a clinician. That is, there is a problem in that a clinician cannot check a 3D medical image from a desire viewpoint.

Accordingly, there is a need for a method that reduces the computational load and the amount of data transfer and also allows a clinician to check a 3D medical image from a desired viewpoint.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, the present invention has been made keeping in mind the above problems occurring in the prior art, and an object of the present invention is to provide an apparatus and method for storing and displaying images in a PACS, which provide a clinician with 2D medical images from a viewpoint desired by the clinician with respect to a 3D medical image, thereby reducing the computational load and the amount of data transfer and also enabling the 3D medical image to be viewed from a desired viewpoint.

More particularly, the present invention is configured to generate a plurality of 2D medical images for a 3D medical image using the reference points of a 3D screen model for the 3D medical image as viewpoints, store the generated 2D medical images together with attribute information related to the generation of the 2D medical images, provide a clinician with the 2D medical images for the 3D medical image when the clinician requests the 3D medical image, and provide a 2D medical image for a desired viewpoint when a clinician switches a viewpoint to the desired viewpoint, thereby reducing the amount of data transfer and also providing a medical image related to the rotation of the 3D medical image in the form of a 2D medical image.

Another object of the present invention is to provide an apparatus and method for storing and displaying images in a PACS, which provide a UI for supporting interaction with the user of a client terminal, and request and display 2D medical images from the various viewpoints of a 3D medical image through the UI, thereby providing convenience to the user and also improving performance.

In accordance with an aspect of the present invention, there is provided an apparatus for storing medical images, including a processor configured to generate a 2D medical image for a 3D medical image at each of reference points of a predetermined 3D screen model; and store the generated 2D medical image along with attribute information related to the generation of the 2D medical image.

The processor may generate the attribute information.

The attribute information may include an identity (ID) of the 2D medical image, information about a reference point of the 2D medical image, and IDs of 2D medical images generated based on adjacent reference points, and may further include a display reference vector indicative of a display criterion for the 2D medical image.

The processor may generate the 2D medical image in a direction from a reference point toward a center point of the 3D screen model.

The processor may set a first reference point in the 3D screen model in accordance with characteristics of a target object of the 3D medical image; and set the reference points based on a relationship with the first reference point. Here, the processor may set the remaining reference points based on a relationship with the first reference point. Reference points spaced apart from the first reference point at a specific interval may be selected as the remaining reference points.

The processor may set a first reference point in the 3D screen model based on a current viewpoint of a user with respect to the 3D medical image.

The processor may set a new origin that is different from a previous center point in the 3D screen model based on a current viewpoint of a user with respect to the 3D medical image. Next, the 2D medical image generated at each of the reference points may be captured in a direction toward a new origin.

In accordance with another aspect of the present invention, there is provided an apparatus for displaying medical images, including a display unit configured to display a first medical image of a plurality of 2D medical images generated using a 3D screen model with respect to a 3D medical image; and a processor configured to receive medical image switching information for the first medical image from a user at a reception unit; and display a second medical image corresponding to the medical image switching information for the first medical image at the display unit.

The processor may display a third medical image corresponding to medical image switching information for the second medical image when the medical image switching information for the second medical image is input to the reception unit.

The processor may extract attribute information for the first medical image from the first medical image; and display the second medical image corresponding to the medical image switching information for the first medical image based on the extracted attribute information when the medical image switching information is received.

The processor may extract IDs of one or more 2D medical images neighboring the first medical image from the attribute information for the first medical image.

Before displaying the second medical image, the processor may modify at least part of the first medical image and display the modified first medical image, or may replace the first medical image with a predetermined substitute image and display the predetermined substitute image, when the medical image switching information is received.

In accordance with yet another aspect of the present invention, there is provided a computer-implemented method, including generating, by a processor, a 2D medical image for a 3D medical image at each of reference points of a predetermined 3D screen model; and storing, by the processor, the generated 2D medical image along with attribute information related to the generation of the 2D medical image to a storage device or a memory.

In accordance with further yet another aspect of the present invention, there is provided a computer-implemented method of displaying medical images, including displaying, by a processor, a first medical image of a plurality of 2D medical images generated using a 3D screen model with respect to a 3D medical image at a display unit; receiving, by the processor, medical image switching information for the first medical image from a user; and displaying, by the processor, a second medical image corresponding to the medical image switching information for the first medical image at the display unit.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Figure 1:
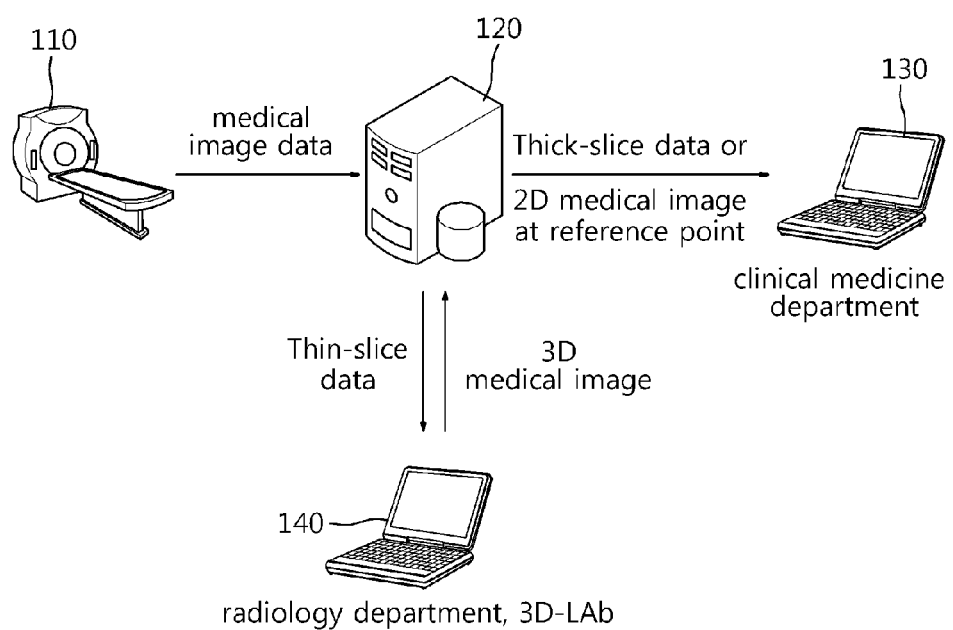
FIG. 1 is a system diagram illustrating an apparatus for storing medical images in accordance with an embodiment of the present invention.

Hereinafter, embodiments of the present invention will be described in detail with reference to the accompanying drawings. Reference now should be made to the elements of drawings, in which the same reference numerals are used throughout the different drawings to designate the same elements. In the following description, detailed descriptions of known elements or functions that may unnecessarily make the gist of the present invention obscure will be omitted.

An apparatus and method for storing and displaying images in a PACS in accordance with embodiments of the present invention will be described in detail with reference to FIGS. 1 to 15.

FIG. 1 is a system diagram illustrating an apparatus for storing medical images in accordance with an embodiment of the present invention.

Referring to FIG. 1, the system includes a medical imaging equipment 110, an apparatus 120 for storing medical images, and client terminals 130 and 140.

The medical imaging equipment 110, for example, a CT apparatus or an MRI apparatus, captures medical images of a patient and provides corresponding medical image data. The medical imaging equipment 110 provides the apparatus 120 for storing medical images with thin-slice data and/or thick-slice data that are generated from the captured raw images.

The thin-slice data and the thick-slice data are a set of two types of image data generated from the same raw image data obtained by the medical imaging equipment 110, that is, a modality. The thin-slice data and the thick-slice data may be selected from the same raw image data based on different criteria, or may be reconstructed based on different reconfiguration rules. The thin-slice data and the thick-slice data may also be regarded as the sets of medical images of different versions of the same raw image data.

In general, the thick-slice data is a set of medical image slices reconstructed at intervals of about 3 to 5 mm, and the thin-slice data is a set of medical image slices reconstructed at intervals of about 0.3 to 1 mm. The thick-slice data can be easily stored and kept, and more detailed data for reading can be obtained from the thin-slice data. In the present invention, an embodiment in which a 3D medical image is generated based on thin-slice data including more detailed data is described as an example, but the contents of the present invention are not limited to the embodiment and numerical values, such as the intervals of the thin-slice data and the thick-slice data.

The apparatus 120 for storing medical images stores medical image data received from the medical imaging equipment 110, receives a 3D medical image generated using the thin-slice data of the medical image data from the client terminal 140 of radiology or a 3D-lab, generates 2D medical images at various viewpoints for the 3D medical image, and stores the 2D medical images.

The apparatus 120 for storing medical images may generate the 2D medical images at various viewpoints for the 3D medical image using a predetermined 3D screen model. In an embodiment, the apparatus 120 for storing medical images may generate a plurality of 2D medical images using directions from respective reference points included in the 3D screen model to the center point of the 3D screen model as viewpoints or may generate a 2D medical image for a reference point by projecting the 3D medical image on a tangent plane that comes into contact with the reference point.

Figure 4:
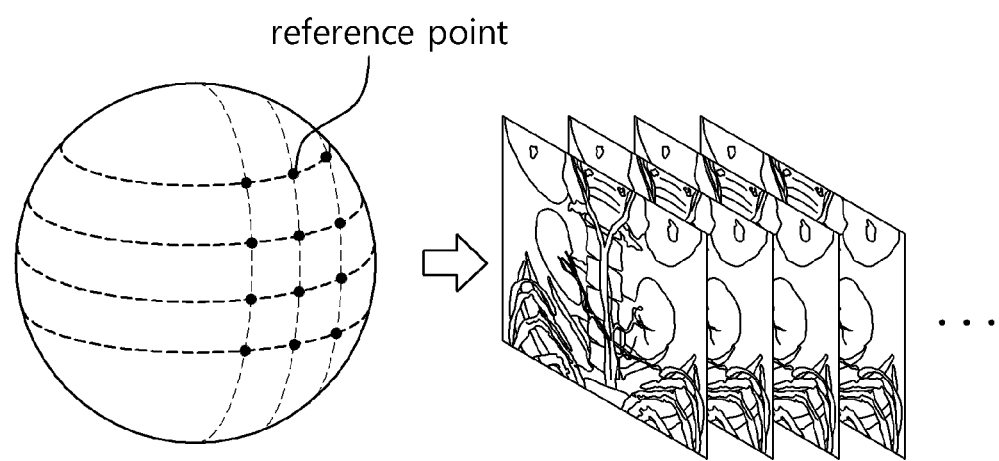
FIG. 4 illustrates a spherical screen model for generating a 2D medical image.
Figure 5:
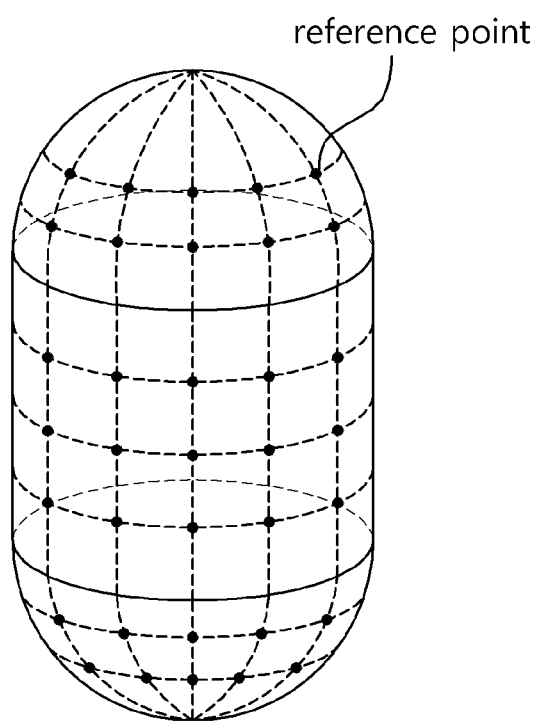
FIG. 5 illustrates a screen model in which a cylinder and hemispheres have been combined to generate a 2D medical image.

As in the examples shown in FIGS. 4 and 5, the 3D screen model may include a spherical screen model, a screen model in which a cylinder and hemispheres are combined, various 3D screen models, or a 3D screen model formed by combining one or more of the various 3D screen models.

As described above, the apparatus 120 for storing medical images may generate the 2D medical images using the 3D screen model. For example, as shown in FIG. 4 illustrating the spherical screen model for generating 2D medical images, the apparatus 120 for storing medical images may generate 2D medical images for the respective reference points of the spherical screen model for a 3D medical image and may generate 2D medical images having the same number of reference points that form the spherical screen model.

Here, the reference point may be 3D coordinates in the spherical screen model, 3D coordinate vectors, or a unit vector or a normal vector vertical to a tangent plane.

After generating the plurality of 2D medical images, the apparatus 120 for storing medical images generates attribute information related to the generation of each of the generated 2D medical images and stores the generated attribute information and the corresponding 2D medical image. When a client terminal, that is, the client terminal 130 of a clinician, requests the 3D medical image, the apparatus 120 for storing medical images provides the plurality of 2D medical images related to the 3D medical image so that switching between the 2D medical images or the changing or movement of the 2D medical images can be easily performed based on the attribute information.

Figure 6:
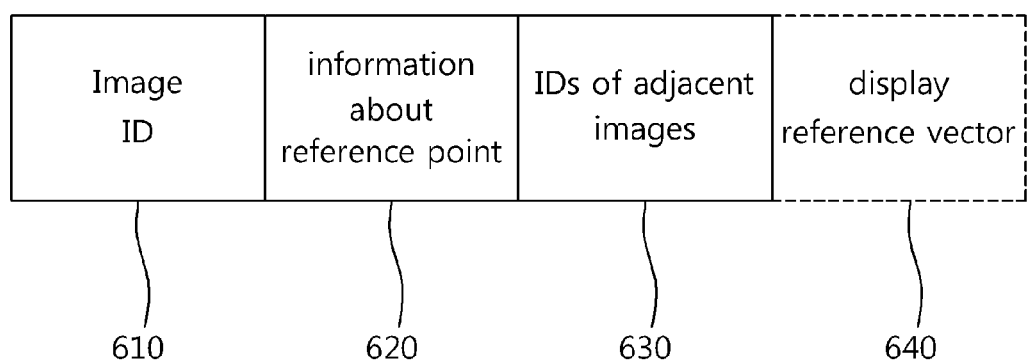
FIG. 6 illustrates an example of a data structure for information about the attributes of a 2D medical image.

As in the example shown in FIG. 6, the attribute information related to the generation of the 2D medical image may include the ID and information about the reference point of the generated 2D medical image, the IDs of 2D medical images neighboring the generated 2D medical image, and a display reference vector indicative of the display criterion for the generated 2D medical image.

In an embodiment, the display reference vector may be optional, and is a reference information for displaying a 2D medical image that is switched when the 2D medical image is switched on a client terminal. Furthermore, the information about the reference point can be one or more of information about 3D coordinates, a 3D coordinate vector, a unit vector, and a normal vector. As though the IDs of neighboring 2D medical images are included in one field as illustrated in the data structure shown in FIG. 6, depending on other examples, each of the IDs of neighboring 2D images may be placed in different fields in accordance with direction of between the 2D medical image and each of the neighboring 2D images. For example, the different fields may include a field for the ID of a 2D medical image in a first direction (right), a field for the ID of a 2D medical image in a second direction (left), a field for the ID of a 2D medical image in a third direction (upper), and a field for the ID of a 2D medical image in a fourth direction (lower).

In the present invention, a data structure indicative of the attribute information of a generated 2D medical image may be included in the DICOM header of the 2D medical image or may be included in a matching table in which 2D medical images are matched with attribute information.

The radiology client terminal 140 receives thin-slice data stored in the apparatus 120 for storing medical images and generates a 3D medical image using the received thin-slice data.

When a radiologist takes a specific action for storing a generated 3D medical image, the radiology client terminal 140 sends the generated 3D medical image to the apparatus 120 for storing medical images, so that the apparatus 120 for storing medical images can store the generated 3D medical image and generate a plurality of 2D medical images for the 3D medical image.

The client terminal 130 of a clinician displays the plurality of 2D medical images using thick-slice data stored in the apparatus 120 for storing medical images. If a radiologist wants to display the generated 3D medical image, the client terminal 130 of a clinician requests the 3D medical image from the apparatus 120 for storing medical images, receives the plurality of 2D medical images for the 3D medical image from the apparatus 120 for storing medical images, and displays the plurality of 2D medical images.

In an embodiment, the plurality of received 2D medical images are medical images generated for the respective reference points of a 3D screen model. The plurality of 2D medical images may be displayed on a screen in response to a user's action using solution software installed in the client terminal 130 of a clinician, and detailed contents thereof are described later with reference to FIG. 3.

Figure 2:
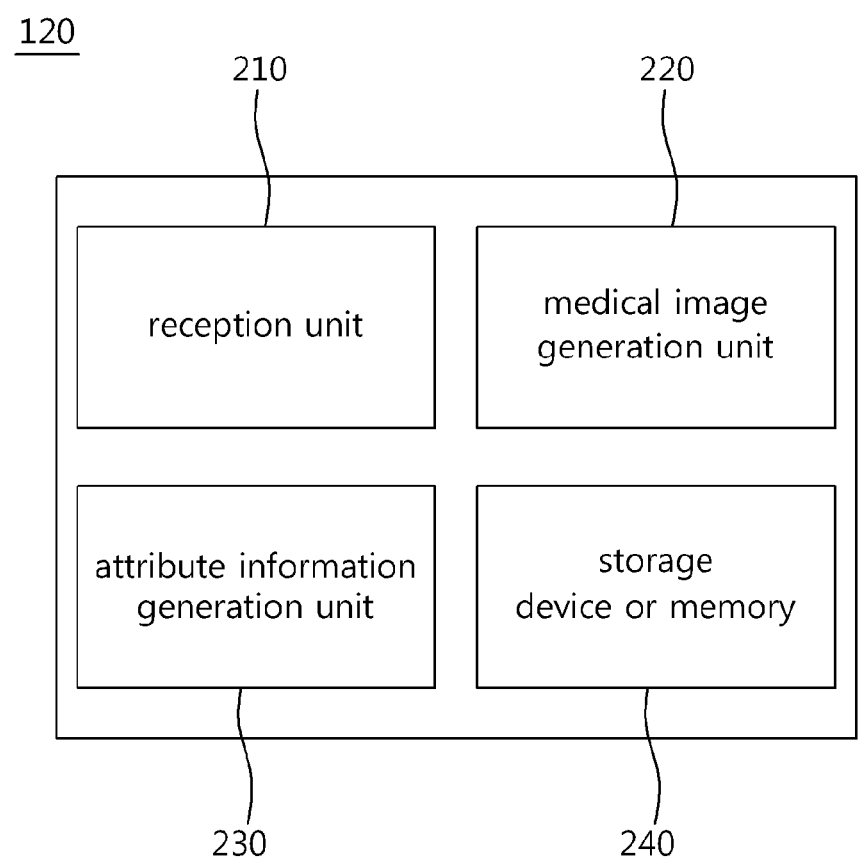
FIG. 2 illustrates the configuration of the apparatus for storing medical images shown in FIG. 1, in accordance with an embodiment of the present invention.

FIG. 2 illustrates a configuration in accordance with an embodiment of the apparatus 120 for storing medical images shown in FIG. 1.

Referring to FIG. 2, the apparatus 120 for storing medical images includes a reception unit 210, a medical image generation unit 220, an attribute information generation unit 230, and a storage device or a memory 240.

The reception unit 210 receives a 3D medical image from the client terminal 140.

The reception unit 210 may receive medical image data from the medical imaging equipment 110 or an external input device, but a description thereof is omitted in order to prevent the description from making the gist of the invention obscure.

The medical image generation unit 220 generates 2D medical images for the 3D medical image, received by the reception unit 210, at the respective reference points of a predetermined 3D screen model.

Here, the medical image generation unit 220 may generate 2D medical images for directions from the respective reference points of the 3D screen model to the center point of the 3D screen model or may generate a 2D medical image for a reference point by projecting the 3D medical image on a tangent plane that comes in contact with the reference point.

The attribute information generation unit 230 generates attribute information for each of the 2D medical images generated by the medical image generation unit 220.

The attribute information is related to the generation of a 2D medical image. The attribute information can include the ID and information about the reference point of the generated 2D medical image, the IDs of 2D medical images neighboring the generated 2D medical image, and a display reference vector.

The storage device or the memory 240 stores the 3D medical image received by the reception unit 210, the plurality of 2D medical images generated by the medical image generation unit 220, and the attribute information generated by the attribute information generation unit 230.

Here, the storage device or the memory 240 may store a 2D medical images including attribute information or may match attribute information with a corresponding 2D medical image and store the matched attribute information and 2D medical image.

Furthermore, the storage device or the memory 240 may store all medical image data, that is, thin-slice data and thick-slice data. A device or storage for storing the thin-slice data and a device or storage for storing the thick-slice data may be formed into one device or may be separately configured.

Figure 3:
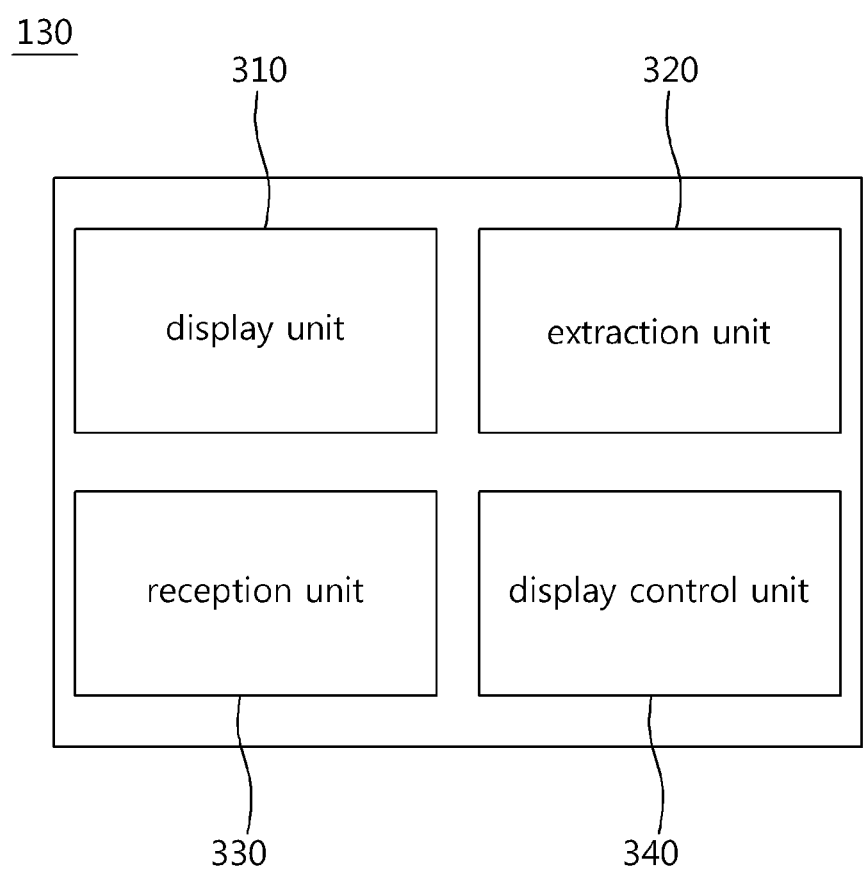
FIG. 3 illustrates the configuration of the client terminal of a clinician shown in FIG. 1, in accordance with an embodiment of the present invention.

FIG. 3 illustrates the configuration of the client terminal 130 of a clinician shown in FIG. 1, in accordance with an embodiment of the present invention. The configuration corresponds to an apparatus for displaying medical images in accordance with the present invention.

It is to be noted that the apparatus for displaying medical images in accordance with the present invention is not limited to the client terminal of a clinical medicine department, but may be applied to all client terminals, workstations, and mobile terminals capable of requesting a 3D medical image stored in the apparatus for storing medical images, for example, a PACS.

Referring to FIG. 3, the client terminal 130 of a clinician includes a display unit 310, an extraction unit 320, a reception unit 330, and a display control unit 340.

The display unit 310 displays a plurality of 2D medical images for a 3D medical image generated by the apparatus for storing medical images using a 3D screen model.

In response to a request for the 3D medical image, the display unit 310 may display a first medical image of the plurality of 2D medical images. The first medical image may be any one predetermined medical image or a randomly determined medical image of the plurality of 2D medical images.

The extraction unit 320 extracts attribute information about the 2D medical image displayed on the display unit 310, for example, the first medical image.

Here, the extraction unit 320 may extract attribute information, such as that shown in FIG. 6, from the DICOM header of the first medical image and may extract attribute information using an additional matching table. In the present invention, it is assumed that attribute information is stored in a DICOM header.

The extraction unit 320 may extract the ID of the first medical image, information about the reference point of the first medical image, the IDs of 2D medical images neighboring the first medical image, and a display reference vector. Here, the display reference vector may be a vector for displaying the first medical image, now being displayed, on a screen. For example, the display reference vector may be a vector regarding how a generated 2D medical image will be displayed, and the display reference vector may include information about which part will be displayed on the upper part.

That is, before the first medical image is displayed on a screen, the extraction unit 320 may extract the display reference vector of the attribute information. The display unit 310 may display the first medical image based on the extracted display reference vector.

The reception unit 330 receives medical image switching information for the first medical image displayed on the display unit 310 from a user, for example, a clinician.

The medical image switching information may be received in response to a command input via an input device included in the client terminal, for example, a mouse or a keyboard. The medical image switching information is information about a movement of a viewpoint to be seen by a user, and may be received in response to an action, such as a directional mouse movement, a mouse wheel operation, or a keyboard direction cursor movement.

Figure 7:
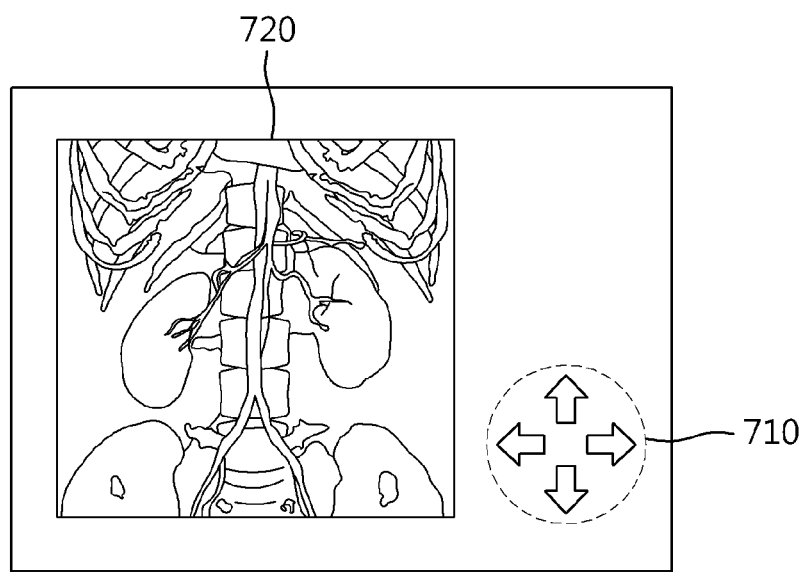
FIG. 7 is a diagram illustrating an example of a display screen in the client terminal of a clinician shown in FIG. 1.

For example, as in an example shown in FIG. 7, when any one 2D medical image 720 for a 3D medical image displayed on the display unit 310 is displayed and a clinician moves a mouse cursor to a User Interface (UI) 710 configured in part of the display unit 310 and places the mouse cursor in a desired viewpoint direction, for example, in any one of the right and left sides and the upper and lower parts, medical image switching information about the corresponding direction is input to the reception unit 330.

In an embodiment, a point of time at which medical image switching information is input may be a point of time at which a mouse cursor is placed over an arrow in a corresponding direction, or a point of time at which a mouse button is clicked at the position of an arrow in the corresponding direction. Furthermore, when medical image switching information is input using the direction keys of a keyboard, a different operation from that of the UI shown in FIG. 7 can be performed.

The display control unit 340 controls the display of a 2D medical image for a 3D medical image. When the medical image switching information is received, the display control unit 340 displays the first medical image, displayed on the display unit 310, as a second medical image corresponding to the medical image switching information using the attribute information extracted by the extraction unit 320.

Figure 8:
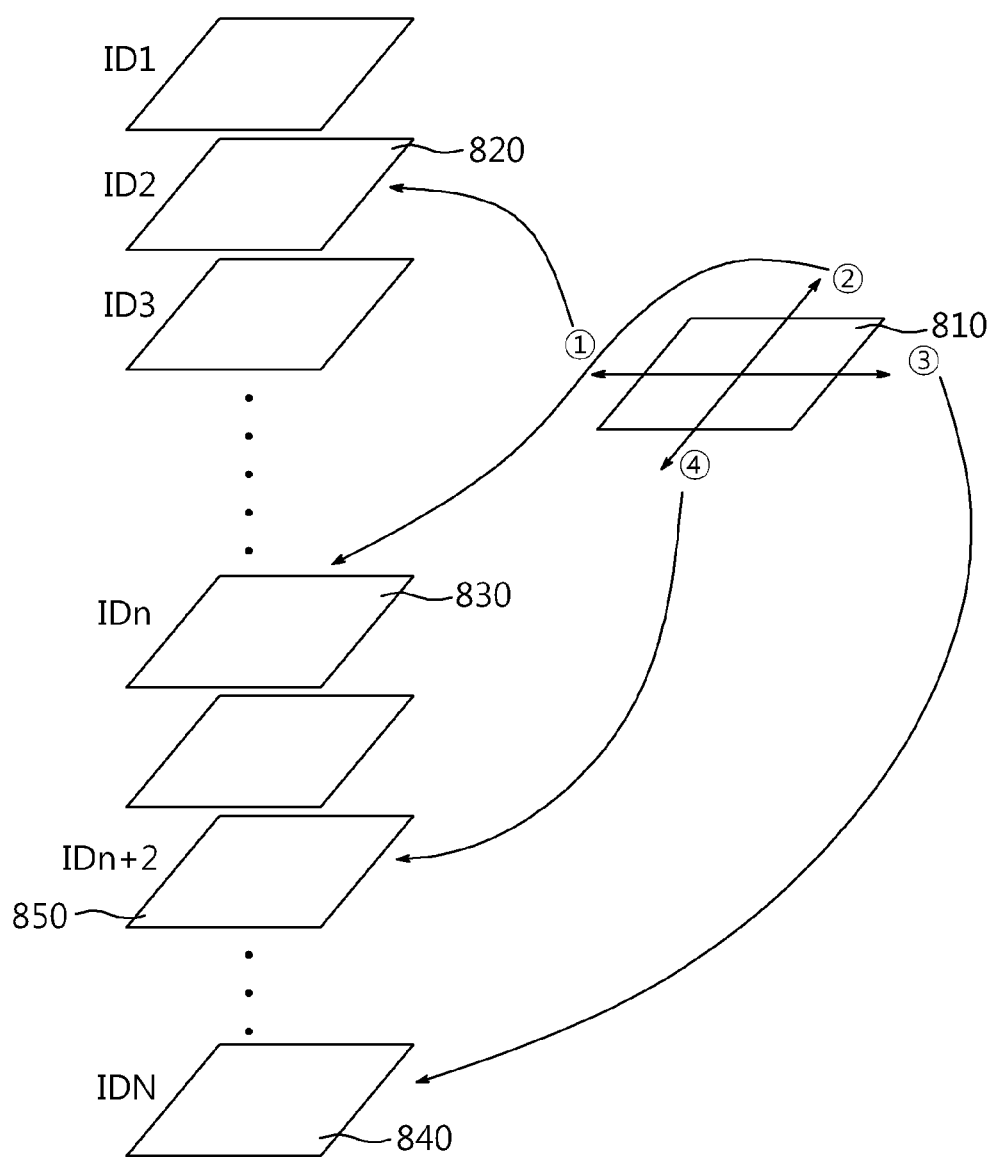
FIG. 8 is a diagram illustrating an example of a process of switching display between 2D medical images for a 3D medical image.

For example, as shown in FIG. 8, it is assumed that 2D medical images having an ID 1 to an ID N for respective reference points have been generated for a 3D medical image. When pieces of medical image switching information □ to □ for a 2D medical image 810 displayed on the display unit 310 are received, the display control unit 340 checks the IDs, that is, ID 2, ID n, ID n+2, and ID N, of 2D medical image 820 to 850 neighboring the 2D medical image 810 corresponding to pieces of medical image switching information, from among the pieces of attribute information for the displayed 2D medical image 810, and displays the pieces of corresponding 2D medical image based on a result of the check. For example, when medical image switching information in the right direction □ is received, the display control unit 340 displays the 2D medical image 850 having the ID N in the display unit 310. When medical image switching information in the left direction □ is received, the display control unit 340 displays the 2D medical image 820 having the ID 2 in the display unit 310.

Likewise, when medical image switching information is received by a clinician in the state in which a second medical image has been displayed on the display unit 310, the display control unit 340 displays a third medical image corresponding to the medical image switching information using attribute information about the second medical image. This process continues to be repeatedly performed.

The display control unit 340 may display a new 2D medical image in the display window of a 2D medical image that is now displayed or may configure an additional display window and display a new 2D medical image in the additional display window. A new 2D medical image preferably is displayed on the same display window as a 2D medical image that is now displayed.

Furthermore, in order to visually provide the switching of a 2D medical image after a clinician's action is received, before displaying a 2D medical image corresponding to medical image switching information after receiving the medical image switching information, the display control unit 340 may modify at least part of a 2D medical image that is now displayed and display the modified image, or may replace a 2D medical image, now being displayed, with a predetermined substitute image and display the predetermined substitute image.

Figure 9A:
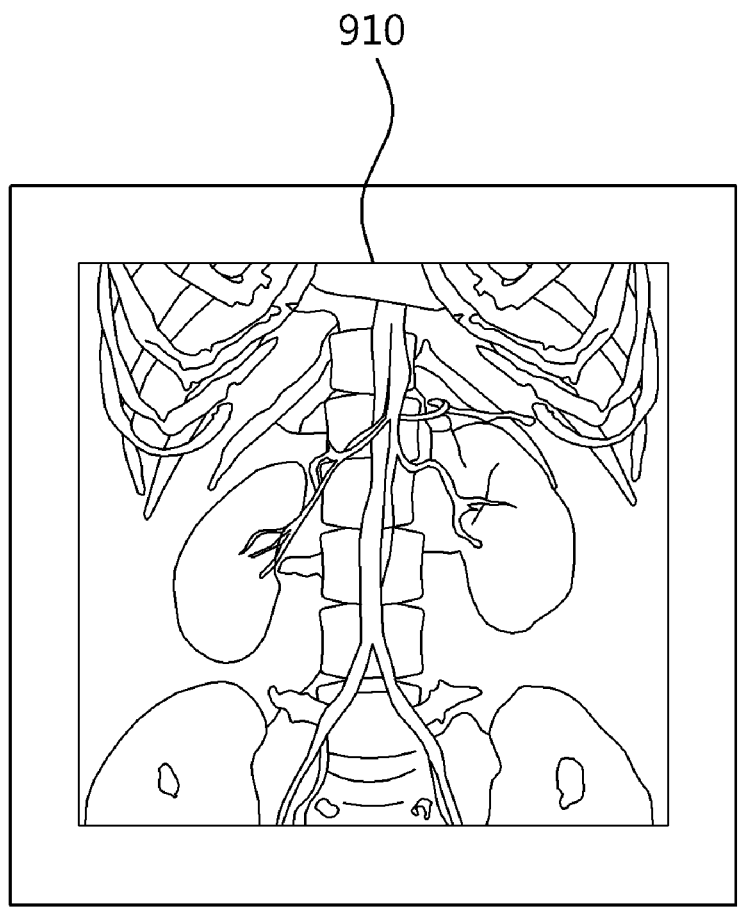
FIGS. 9A, 9B, and 9C are diagrams visually illustrating an example of a process of switching between 2D medical images.
Figure 9B:
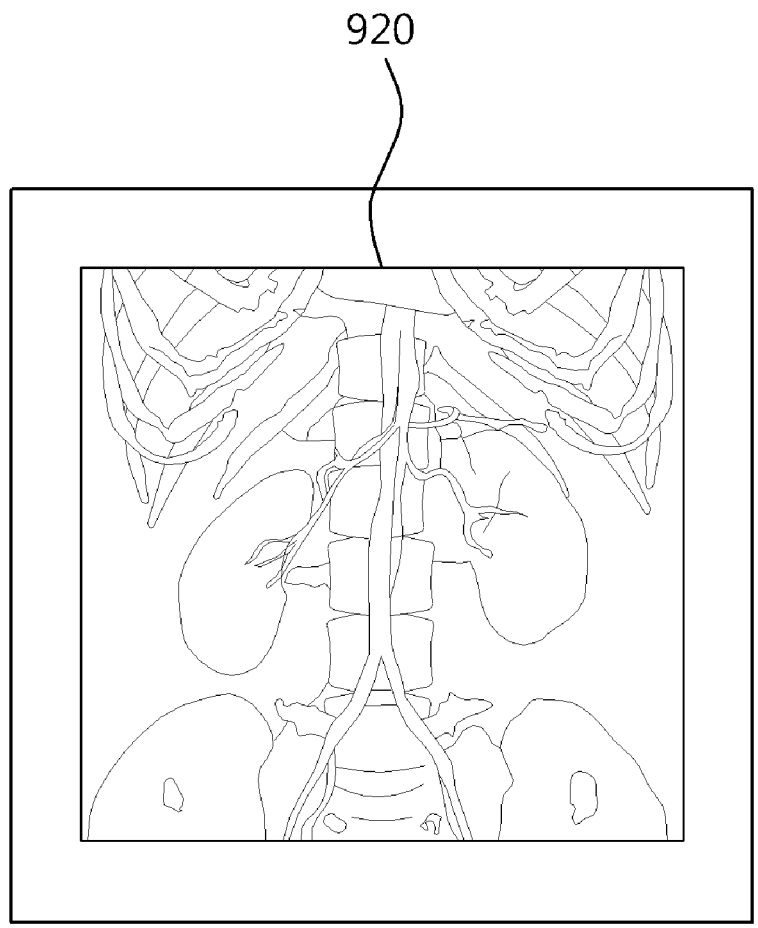
Figure 9C:
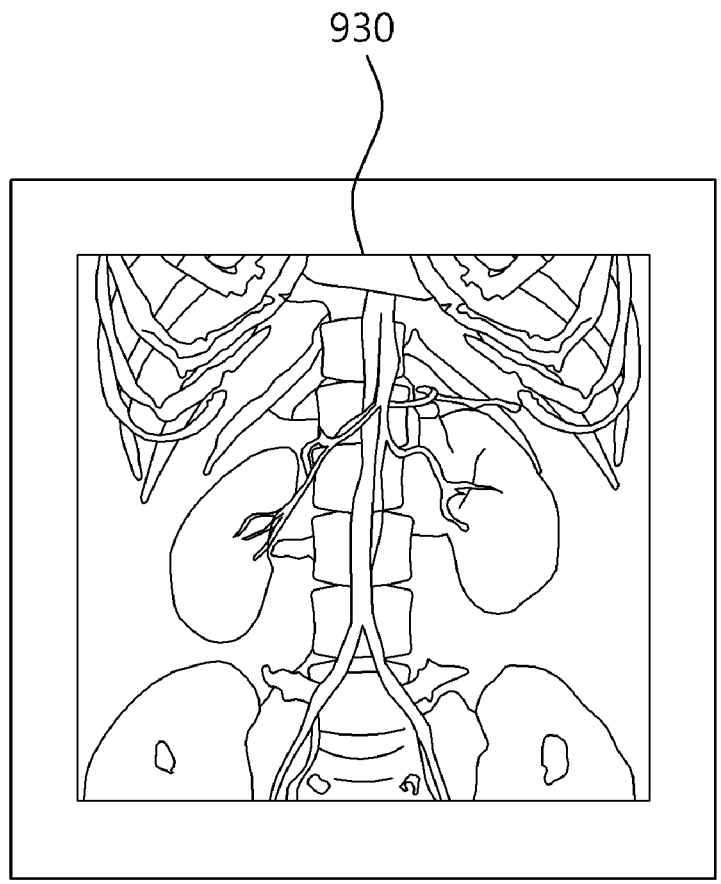

For example, as in an example shown in FIG. 9A to FIG. 9C, when medical image switching information is received in the state in which a first medical image 910 has been displayed, the display control unit 340 may modify at least part of the first medical image 910, display the modified first medical image 920, and display a second medical image 930 corresponding to the medical image switching information using attribute information about the first medical image 910. In an embodiment, the display control unit 340 may replace the medical image 920 of FIG. 9B with a predetermined substitute image and display the predetermined substitute image.

In an embodiment, the display control unit 340 may generate a 2D medical image corresponding to an intermediate image between a first medical image and a second medical image in a process of switching the first medical image into the second medical image, if necessary, and display the generated 2D medical image. In another embodiment, an intermediate image may be generated using two medical images, neighboring 2D medical images, various methods of generating the intermediate image, or one or more of the various methods.

As described above, the apparatus for storing medical images in accordance with the present invention generates a plurality of 2D medical images for a 3D medical image using a predetermined 3D screen model and stores the generated 2D medical images and pieces of corresponding attribute information. Accordingly, the amount of data transfer can be reduced because only a 2D medical image is provided to a clinician without directly providing a 3D medical image to the clinician, and the capacity of memory can also be reduced because the computational load in accordance with a change of a 3D viewpoint can be reduced.

Furthermore, the apparatus for displaying medical images in accordance with the present invention can provide similar performance to the rotation of a 3D medical image because it can provide a 3D medical image for a viewpoint desired by a user, that is, a 2D medical image generated at a corresponding reference point, owing to the advantages. Furthermore, the apparatus for displaying medical images in accordance with the present invention can rapidly display a medical image at a corresponding viewpoint because only a 2D medical image is provided and thus provide a user with convenience because a delay time taken to display a medical image for a clinician can be reduced.

Figure 10:
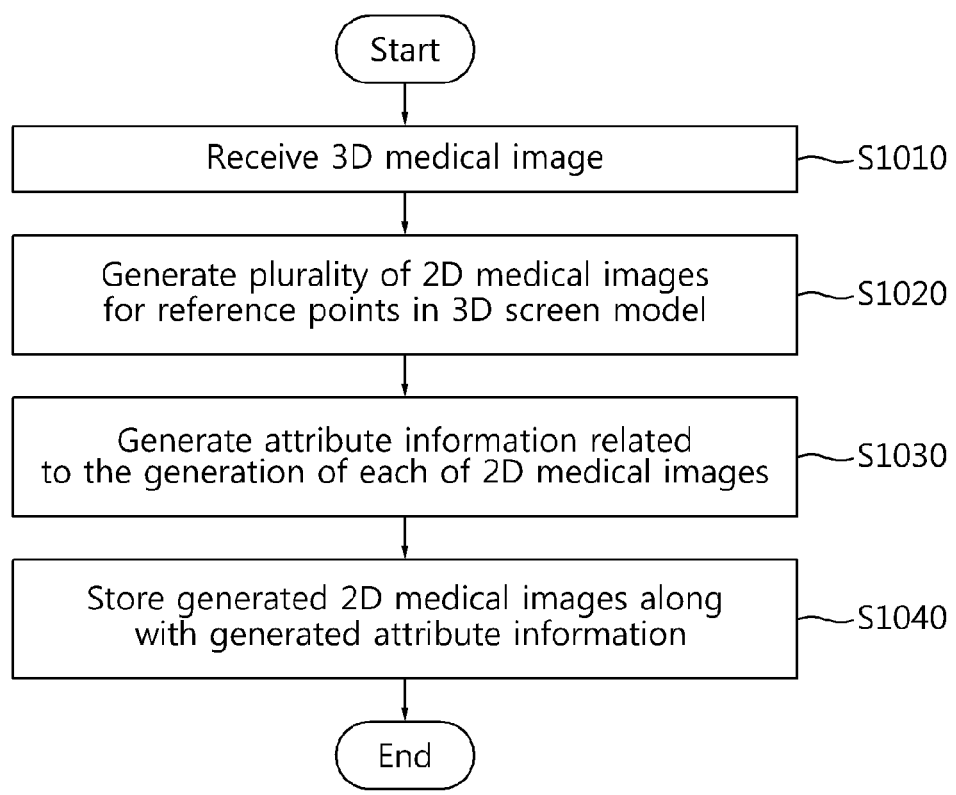
FIG. 10 is a flowchart illustrating a method of storing medical images in accordance with an embodiment of the present invention.

FIG. 10 is a flowchart illustrating a method of storing medical images in accordance with an embodiment of the present invention. The method of FIG. 10 corresponds to an operation performed by the apparatus for storing medical images shown in FIG. 1.

Referring to FIG. 10, in the method of storing medical images, first, a 3D medical image generated by the client terminal of a radiologist or 3D-lab using thin-slice data is received at step S1010.

In an embodiment, the received 3D medical image may be stored in the apparatus for storing medical images or an additional storage.

When the 3D medical image is received, a plurality of 2D medical images for the received 3D medical image is generated. The plurality of 2D medical images for the 3D medical image is generated using a predetermined 3D screen model at step S1020.

Here, the 3D screen model includes reference points set at equal intervals, specific locations, specific coordinates, or specific viewpoints up and down and left and right. The plurality of 2D medical images for the 3D medical image can be generated using the reference points. For example, a 2D medical image using a direction from a reference point to the center point of the 3D screen model as a viewpoint may be generated, and a 2D medical image at a reference point may be generated by projecting the 3D medical image on a tangent plane that comes into contact with the reference point. Furthermore, those skilled in the art can apply, modify, and practice various methods in addition to the methods.

After the plurality of 2D medical images is generated, each of attribute information related to the generation of the respective 2D medical images is generated at step S1030.

The attribute information is related to the generation of a 2D medical image, and the attribute information may include the ID and information about the reference point of the 2D medical image, the IDs of neighboring 2D medical images, and a display reference vector. The display reference vector may be used as reference information for displaying the 2D medical image in the client terminal of a clinician.

After the plurality of 2D medical images and the attribute information about each of the 2D medical images are generated, the generated 2D medical images are stored along with each of generated attribute information at step S1040.

The attribute information may be stored in the DICOM header of a corresponding 2D medical image, and the attribute information may have the same data structure as that of FIG. 6.

In an embodiment, it is evident that the 3D medical image is associated with the plurality of 2D medical images generated using the 3D screen model.

Figure 11:
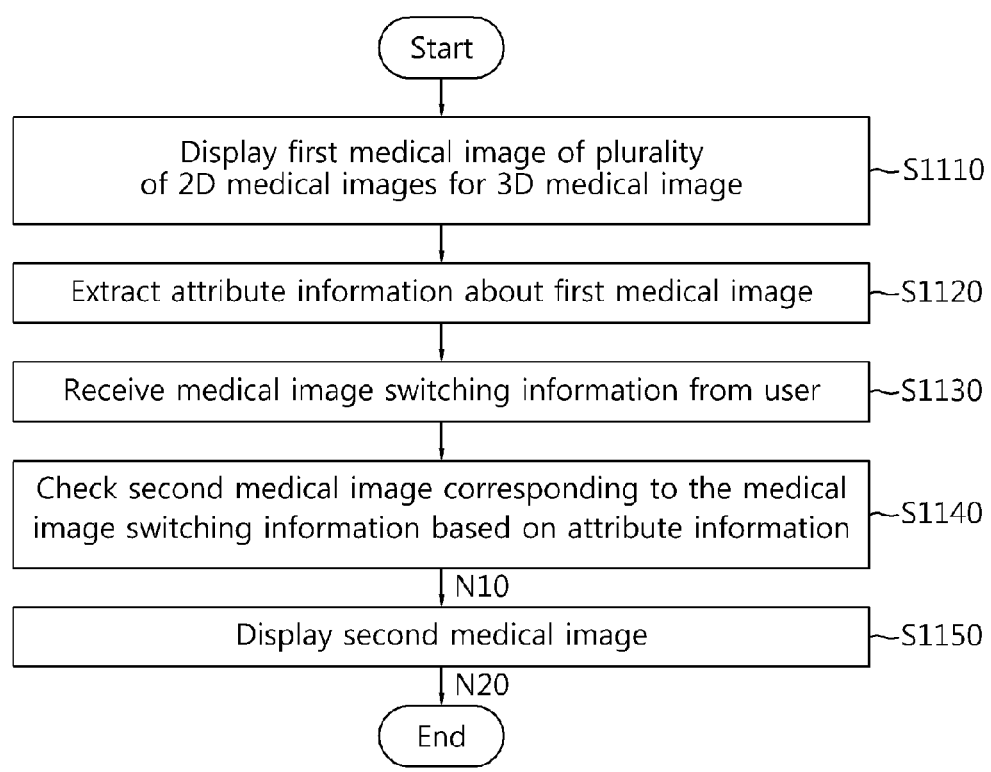
FIG. 11 is a flowchart illustrating a method of displaying medical images in accordance with an embodiment of the present invention.

FIG. 11 is a flowchart illustrating a method of displaying medical images in accordance with an embodiment of the present invention. The method of FIG. 11 corresponds to an operation performed by the client terminal of a clinical medicine department shown in FIG. 1. It is to be noted that the method of displaying medical images is not limited to the client terminal of a clinical medicine department and may be applied to all client terminals, workstations, and mobile terminals capable of requesting a 3D medical image stored in the apparatus for storing medical images, for example, a PACS.

Referring to FIG. 11, in the method of displaying medical images, first, a 3D medical image is requested from the apparatus for storing medical images, for example, a PACS. A first medical image of a plurality of 2D medical images for the 3D medical image, is received from the apparatus for storing medical images and displayed at step S1110.

In some embodiments, all the plurality of 2D medical images for the 3D medical image may be received and stored, and the first medical image may then be displayed.

The plurality of 2D medical images is generated using a predetermined 3D screen model and may be medical images generated from the 3D medical image using the reference points of the 3D screen model, for example, reference points, formed at specific intervals or specific locations up and down and left and right, as viewpoints.

When the first medical image is displayed on a screen of the display unit 310, attribute information about the first medical image is extracted at step S1120.

The attribute information extracted at step S1120 may include the IDs of 2D medical images neighboring the first medical image.

In an embodiment, the attribute information may be extracted before displaying the first medical image, and the first medical image may be displayed on a screen based on a display reference vector included in the extracted attribute information. In this case, some of the attribute information may be extracted before displaying the first medical image.

After the attribute information is extracted, medical image switching information is received from a user at step S1130.

The medical image switching information corresponds to the input of a user who wants to see the 3D medical image at a different viewpoint. The medical image switching information may include all pieces of information related to the switching of a medical image, such as an action using a mouse and an action using a keyboard.

After the medical image switching information is received, a second medical image corresponding to the medical image switching information, that is, a second medical image corresponding to the medical image switching information, from among the plurality of 2D medical images for the 3D medical image, is checked based on the attribute information about the first medical image extracted at step S1120, at step S1140. The checked second medical image is displayed on a screen of the display unit 310 at step S1150.

Here, the second medical image may be displayed on a region in which the first medical image is now displayed. If switching from the first medical image to the second medical image is delayed, the switching process may be visually transferred to a user. This is described later with reference to FIG. 12.

Figure 12:
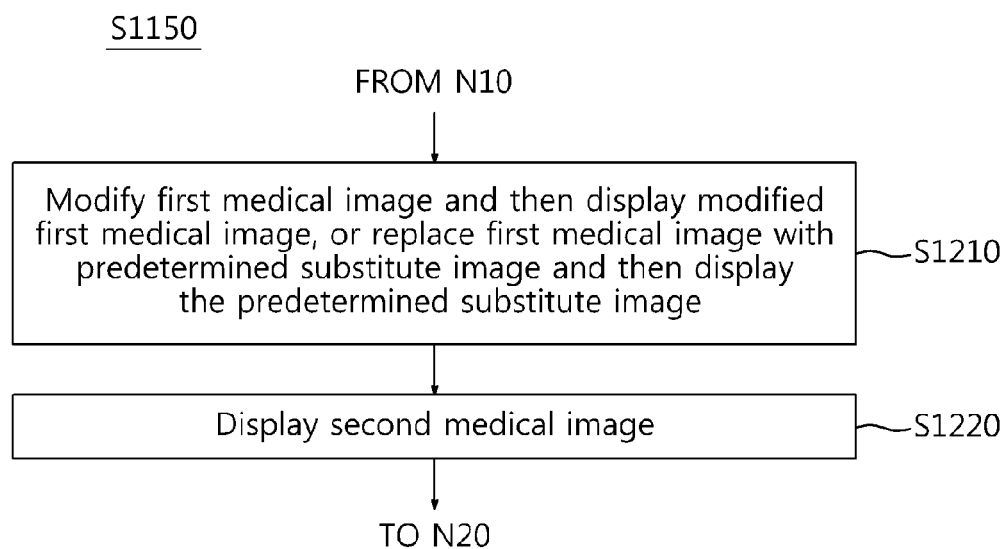
FIG. 12 is a flowchart illustrating step S1150 shown in FIG. 11, in accordance with an embodiment of the present invention.

FIG. 12 is a flowchart illustrating step S1150 shown in FIG. 11, in accordance with an embodiment of the present invention.

Referring to FIG. 12, displaying the second medical image at step S1150 may include modifying the first medical image that is now displayed and displaying the modified first medical image, or replacing the first medical image with a predetermined substitute image and displaying the predetermined substitute image, before displaying the second medical image, at step S1210.

Here, in the present invention, part of or the entire first medical image may be modified and displayed using a predetermined method. The predetermined method may be an algorithm related to image processing.

After displaying the modified first medical image or the substitute image before displaying the second medical image or for a specific time, the modified first medical image or the substitute image is replaced with the second medical image and the replaced second medical image is displayed at step S1220.

In accordance with this process, a user may know that a medical image is being switched although a specific delay time occurs.

It is to be noted that the process of switching a medical image is not limited to the above-described method and a user may be informed of the process of switching a medical image using other methods.

For example, in accordance with the present invention, a user may be visually informed of a process of switching a medical image by displaying an intermediate image, generated using a first medical image and a second medical image, or an intermediate image, generated using a first medical image and images neighboring the first medical image, between the first medical image and the second medical image.

Figure 13:
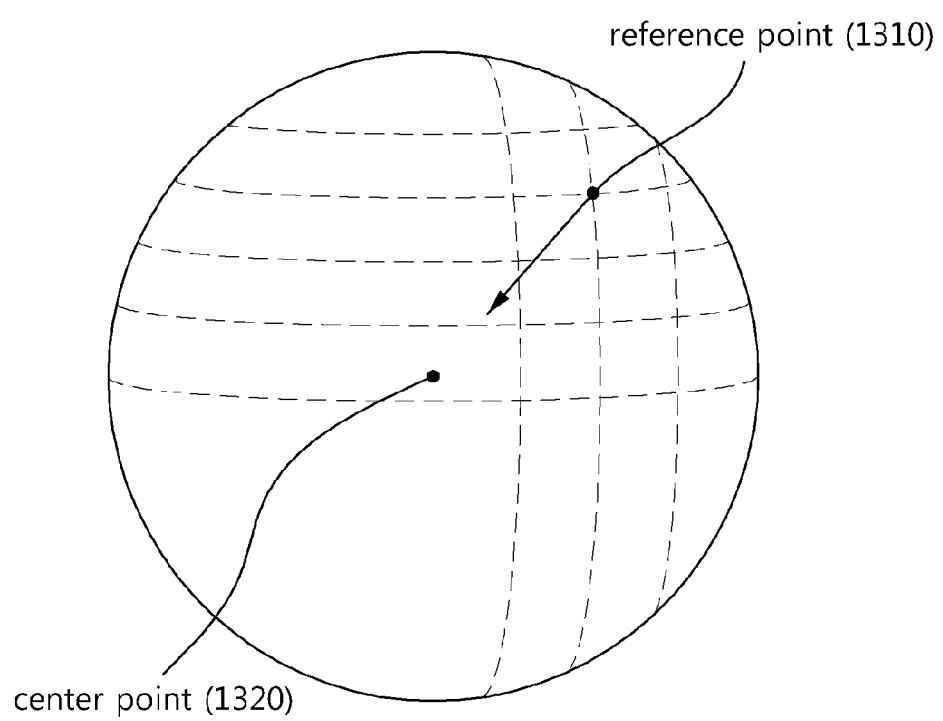
FIG. 13 is a diagram illustrating an example of a method of generating a medical image in accordance with an embodiment of the present invention.

FIG. 13 is a diagram illustrating an example of a method of generating a medical image in accordance with an embodiment of the present invention.

FIG. 13 illustrates an example in which a first 2D medical image is captured in a direction from a first reference point 1310 to a center point 1320 within a 3D screen model.

A user may select the first reference point 1310 as an optimized point that is most advantageous in identifying a target object in accordance with the characteristics of the target object of the 3D medical image. The optimized first reference point 1310 may be determined by the medical image generation unit 220 depending on the type of organ of the target object, modality, the type of medical imaging equipment and/or the type of lesion to be monitored.

Here, the medical image generation unit 220 may select the first reference point 1310 using a knowledge-based scheme with reference to a medical image generation history previously selected in accordance with the characteristics of the target object. The previously selected medical image generation history may mean the recording of the positions or directions of reference viewpoints that were selected by a plurality of users when generating and storing medical images for the target object.

Meanwhile, the 2D medical image may be captured and generated from each of a plurality of reference points in a direction toward the center point within the 3D screen model, but the direction is not limited to the center point of the 3D screen model. Another embodiment in which a reference direction or the origin for generating a 2D medical image is generated is shown in FIG. 14.

Figure 14:
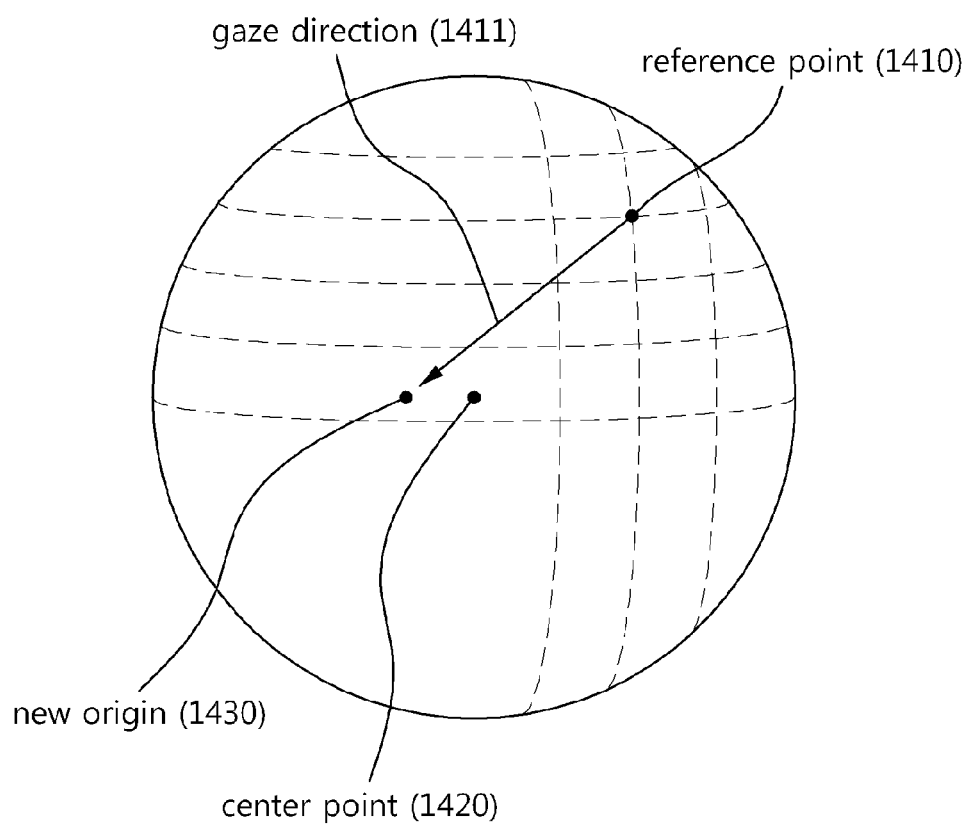
FIG. 14 is a diagram illustrating an example of a method of generating a medical image in accordance with another embodiment of the present invention.

FIG. 14 is a diagram illustrating an example of a method of generating a medical image in accordance with another embodiment of the present invention.

FIG. 14 illustrates an example in which a 2D medical image is captured in a direction from a first reference point 1410 to a new origin 1430.

The medical image generation unit 220 may set a new origin 1430 by taking a gaze direction 1411 seen by a user into consideration at a current viewpoint at which the user wants to capture, generate, and store a 2D medical image. That is, if the gaze direction 1411 now seen by the user is not directed from the reference point 1410 to a previous center point 1420, but is directed in a different direction, the medical image generation unit 220 may select one point on the gaze direction 1411 as the new origin 1430.

Here, the medical image generation unit 220 may set a specific volume region in the central part of a 3D screen model and set the new origin 1430 within the volume region by taking a relation between the new origin 1430 and the gaze direction 1411 into consideration. In another embodiment, the medical image generation unit 220 may select a point having the shortest distance between the point and the center point 1420, from among points on the gaze direction 1411, as the new origin 1430.

Here, the medical image generation unit 220 may capture and generate a 2D medical image for each of one or more reference points on a 3D screen model in a direction toward the new origin 1430, not toward a previous center point 1420.

Furthermore, the medical image generation unit 220 may take the gaze direction 1411 that is now seen by a user into consideration as a criterion for selecting the first reference point 1410. That is, the medical image generation unit 220 may select the first reference point 1410 with reference to the gaze direction 1411 that is now seen by a user who wants to capture, generate, and store a 2D medical image. In an embodiment, an interaction where the gaze direction 1411 meets the 3D screen model may be selected as the first reference point 1410, and points spaced apart from the first reference point 1410 at a specific interval may be selected as the remaining reference points. In another embodiment, a reference point closest to an interaction where the gaze direction 1411 meets the 3D screen model, from among reference points on a predetermined grid on the 3D screen model, may be selected as the first reference point 1410.

In this case, there is an advantage in that a set of 2D medical images are generated so that the direction of an image now seen by a user can be seen at the client terminal without change.

Figure 15:
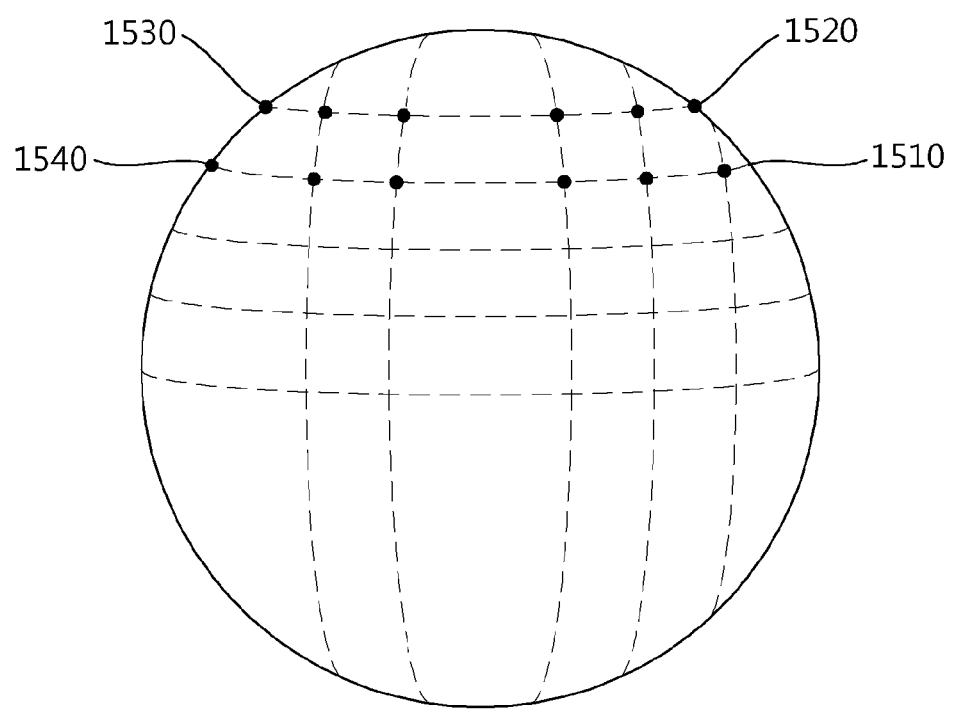
FIG. 15 is a diagram illustrating the reference points of a 3D screen model in accordance with yet another embodiment of the present invention.

FIG. 15 is a diagram illustrating the reference points of a 3D screen model in accordance with yet another embodiment of the present invention.

Referring to FIG. 15, there are shown reference points 1510, 1520, 1530, and 1540 on a 3D screen model.

If a user selects a 2D medical image generated at the reference point 1510, the 2D medical image generated at the reference point 1510 is displayed. Next, if a user sequentially selects the reference point 1520, the reference point 1530, and the reference point 1540, 2D medical images generated at the reference point 1520, the reference point 1530, and the reference point 1540, respectively, will be displayed.

Here, if the display directions of the 2D medical images generated at the respective reference points have not yet been determined, the up and down and left and right directions in which the 2D medical images are displayed may be changed depending on a sequence in which a user selects the reference points 1510, 1520, 1530, and 1540.

Accordingly, the reference points 1510, 1520, 1530, and 1540 are identified along with their positions, coordinates, or direction vectors on the 3D screen model, and each of the reference points 1510, 1520, 1530, and 1540 may further include a display reference vector as described above. A more intuitive example of this display reference vector may include an up vector indicative of the upward direction of an image. That is, each of the reference points may previously include information about a reference direction for the up and down and left and right directions in which a captured image will be displayed. The information about the reference direction of each reference point may be derived from the position, coordinates, or direction vector of the reference point in accordance with a specific rule.

As described above, information about a display criterion direction (or a display reference vector) included at each of reference points may influence the direction of a 2D medical image generated when the medical image generation unit 220 generates the 2D medical image at each of the reference points.

In particular, if 2D medical images overlap each other in a predetermined shape, such as a rectangle, an oval, or a circle, the medical image generation unit 220 captures a 2D medical image generated at each of reference points based on information about a display criterion direction.

The computer-implemented method of processing, generating, and storing medical images and/or the method of computer-implemented displaying medical images in accordance with the embodiments of the present invention may be implemented in the form of program instructions that are executable by various types of computer means, and may be recorded in a computer-readable storage medium. The computer-readable storage medium may include program instructions, data files, and data structures either independently or in combination. The program instructions stored in the medium may be designed and configured especially for the present invention or may be known to and usable by those skilled in the art of computer software. Examples of the computer-readable storage medium may include a magnetic medium, such as a hard disk, a floppy disk, or magnetic tape, an optical medium, such as CD-ROM or a DVD, a magneto-optical medium, such as a floptical disk, and a hardware apparatus, such as ROM, RAM, or flash memory which is especially configured to store and execute the program instructions. Examples of the program instructions include not only such machine language code that is created by a compiler, but also such high-level language code that is executable by a computer using an interpreter or the like. The hardware apparatus can be configured to function as one or more software modules so as to perform the operation of the present invention, and vice versa.

The reception unit 210, the medical image generation unit 220, the attribute information generation unit 230, the extraction unit 320, the reception unit 330, and the display control unit 340 may be implemented as one or more processors which run or execute the computer-implemented methods of the examples of the present invention.

In accordance with the present invention, 2D medical images for a 3D medical image are generated using reference points, set at the 3D positions of a 3D screen model, as viewpoints, and the plurality of generated 2D medical images is stored along with attribute information related to the generation of the 2D medical images. Accordingly, the present invention has the advantage of providing an effect whereby a 3D medical image is seemingly rotated using 2D medical images.

Here, the attribute information may include information about a reference point for generating a 2D medical image in a 3D medical image, for example, information about a direction vector, the ID of the generated 2D medical image, and the IDs of 2D medical images corresponding to adjacent reference points that can be switched between, moved, or changed in response to interaction with a user. The attribute information may further include a display reference vector, that is, a criterion when the 2D medical image is displayed on a client terminal. Accordingly, there are advantages in that switching and changing between a plurality of 2D medical images can be easily performed using a 3D screen model and the amount of data transfer and memory required can be reduced because a 3D medical image is displayed using 2D medical images.

Furthermore, the present invention is advantageous in that a user can check a 3D medical image from a desired viewpoint by providing a UI for performing interaction with the user, such as switching or changing between a plurality of 2D medical images generated using a 3D screen model, and user convenience can be provided and the performance of a system or apparatus can be improved because viewpoints can be switched between using an input device, such as a mouse or a keyboard.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for storing medical images, comprising:
   a processor configured to:
      generate a two-dimensional (2D) medical image for a three-dimensional (3D) medical image at each of reference points of a predetermined 3D screen model in a direction from a reference point toward a center point of the 3D screen model; and
      store the generated 2D medical image along with attribute information related to the generation of the 2D medical image to a storage device or a memory.

2. The apparatus of claim 1, wherein the processor is further configured to generate the attribute information.

3. The apparatus of claim 1, wherein the attribute information comprises:
   an identity (ID) of the 2D medical image,
   information about a reference point of the 2D medical image, and
   IDs of 2D medical images generated based on adjacent reference points.

4. The apparatus of claim 3, wherein the attribute information further comprises a display reference vector indicative of a display criterion for the 2D medical image.

5. An apparatus for storing medical images, comprising:
   a processor configured to:
      generate a two-dimensional (2D) medical image for a three-dimensional (3D) medical image at each of the reference points of a predetermined 3D screen model:
      store the generated 2D medical image along with attribute information related to the generation of the 2D medical image device or a memory;

set a first reference point in the 3D screen model in accordance with characteristics of a target object of the 3D medical image; and set the reference points based on a relationship with the first reference point.

6. The apparatus of claim 5, wherein the processor is further configured to:

analyze the characteristics of the target object of the 3D medical image and a previous medical image generation history; and set the first reference point based on results of the analysis.

7. The apparatus of claim 1, wherein the processor is further configured to set a first reference point in the 3D screen model based on a current viewpoint of a user with respect to the 3D medical image.

8. The apparatus of claim 1, wherein the processor is further configured to set a new origin that is different from a previous center point in the 3D screen model based on a current viewpoint of a user with respect to the 3D medical image.

9. An apparatus for displaying medical images, comprising:

a display unit configured to display a first medical image of a plurality of 2D medical images generated using a 3D screen model with respect to a 3D medical image; and a processor configured to:
receive medical image switching information for the first medical image from a user via a user interface;
display a second medical image corresponding to the medical image switching information for the first medical image at the display unit; and
display a third medical image corresponding to medical image switching information for the second medical image when the medical image switching information for the second medical image input to the reception unit.

10. The apparatus of claim 9, wherein the processor is further configured to:
extract attribute information for the first medical image from the first medical image; and
display the second medical image corresponding to the medical image switching information for the first medical image based on the extracted attribute information when the medical image switching information is received.

11. The apparatus of claim 10, wherein the processor is further configured to extract IDs of one or more 2D medical images neighboring the first medical image from the attribute information for the first medical image.

12. The apparatus of claim 9, wherein the processor is further configured to:
before displaying the second medical image, modify at least part of the first medical image and display the modified first medical image, or
replace the first medical image with a predetermined substitute image and display the predetermined substitute image, when the medical image switching information is received.

13. A computer-implemented method, comprising:
generating, by a processor, a 2D medical image for a 3D medical image at each of reference points of a predetermined 3D screen model;

storing, by the processor, the generated 2D medical image along with attribute information related to the generation of the 2D medical image to a storage device or a memory; and setting, by the processor, a first reference point in the 3D screen model based on a current viewpoint of a user with respect to the 3D medical image.

14. The method of claim 13, further comprising generating, by the processor, the attribute information, wherein
the storing further comprises storing both the generated attribute information and a 2D medical image corresponding to the attribute information to the storage device or the memory.

15. The method of claim 13, wherein the attribute information comprises:
an ID of the 2D medical image,
information about a reference point of the 2D medical image,
IDs of 2D medical images generated based on adjacent reference points, and
a display reference vector indicative of a display criterion for the 2D medical image.

16. The method of claim 13, further comprising:
setting, by the processor, reference point in the 3D screen model in accordance with characteristics of a target object of the 3D medical image; and
setting, by the processor, the reference points based on a relationship with the first reference point.

17. The method of claim 13, wherein the generating comprises:
setting, by the processor, a new origin that is different from a previous center point in the 3D screen model based on a current viewpoint of a user with respect to the 3D medical image; and
generating, by the processor, the 2D medical image in a direction from each of the reference points to the new origin.

18. A computer-implemented method, comprising:
displaying, by a processor, a first medical image of a plurality of 2D medical images generated using a 3D screen model with respect to a 3D medical image at a display unit;
receiving, by the processor, medical image switching information for the first medical image from a user;
displaying, by the processor, a second medical image corresponding to the medical image switching information for the first medical image at the display unit; and
extracting, by the processor, attribute information for the first medical image from the first medical image,
wherein the displaying of the second medical image further comprises displaying the second medical image based on the extracted attribute information at the display unit when the medical image switching information is received.

19. The method of claim 18, wherein the displaying of the second medical image further comprises:
before displaying the second medical image, modifying at least part of the first medical image and displaying the modified part of the first medical image, or
replacing the first medical image with a predetermined substitute image and displaying the predetermined substitute image, when the medical image switching information is received.

20. A non-transitory computer-readable storage medium having stored therein program instructions, which when executed by a processor, cause the processor to:

generate a 2D medical image for a 3D medical image at each of reference points of a predetermined 3D screen model;
store the generated 2D medical image along with attribute information related to the generation of the 2D medical image to a storage device or a memory; and
set a first reference point in the 3D screen model based on a current viewpoint of a user with respect to the 3D medical image.

21. A non-transitory computer-readable storage medium having stored therein program instructions, which when executed by a processor, cause the processor to:
display a first medical image of a plurality of 2D medical images generated using a 3D screen model with respect to a 3D medical image at a display unit;
receive medical image switching information for the first medical image from a user;
display a second medical image corresponding to the medical image switching information for the first medical image at the display unit; and
extract attribute information for the first medical image from the first medical image,
wherein the processor displays the second medical image based on the extracted attribute information at the display unit when the medical image switching information is received.

* * * * *